US012686839B2

(12) United States Patent
Hou et al.

(10) Patent No.: US 12,686,839 B2
(45) Date of Patent: Jul. 21, 2026

(54) DETECTION CHIP AND MANUFACTURING METHOD THEREFOR, AND REACTION SYSTEM

(71) Applicant: BOE Technology Group Co., Ltd., Beijing (CN)

(72) Inventors: Mengjun Hou, Beijing (CN); Zijian Zhao, Beijing (CN); Yudan Yin, Beijing (CN); Zongmin Liu, Beijing (CN); Liye Duan, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 1072 days.

(21) Appl. No.: 17/780,251

(22) PCT Filed: Jan. 14, 2021

(86) PCT No.: PCT/CN2021/071681
§ 371 (c)(1),
(2) Date: May 26, 2022

(87) PCT Pub. No.: WO2021/169650
PCT Pub. Date: Sep. 2, 2021

(65) Prior Publication Data
US 2022/0411732 A1 Dec. 29, 2022

(30) Foreign Application Priority Data

Feb. 26, 2020 (CN) .......................... 202010121512.9

(51) Int. Cl.
*C12M 1/32* (2006.01)
*C12M 1/34* (2006.01)
(52) U.S. Cl.
CPC .................................... *C12M 1/34* (2013.01)

(58) Field of Classification Search
CPC ........................ B01L 2300/0829; C12M 23/12
See application file for complete search history.

(56) References Cited

U.S. PATENT DOCUMENTS

2004/0022677 A1* 2/2004 Wohlstadter ......... G01N 21/253
422/52
2006/0000709 A1 1/2006 Bohm et al.
(Continued)

FOREIGN PATENT DOCUMENTS

CN 1715930 A 1/2006
CN 102168011 A 8/2011
(Continued)

OTHER PUBLICATIONS

CN202010121512.9 first office action.
(Continued)

*Primary Examiner* — Jonathan M Hurst
(74) *Attorney, Agent, or Firm* — IPro, PLLC

(57) ABSTRACT

Disclosed are a detection chip and a manufacturing method therefor, and a reaction system. The detection chip includes: a first substrate (11); a microcavity defining layer (12), which is located on the first substrate (11) and defines a plurality of micro-reaction chambers (120); and a shading structure layer (13), which is located on the first substrate (11) and provided among the plurality of micro-reaction chambers (120). In practical application, the number of target molecules in a reaction system solution in each micro-reaction chamber (120) can be determined by collecting a fluorescence image; and the detection chip is provided with the shading structure layer (13), and the shading structure layer (13) is located on the first substrate (11) and provided among the plurality of micro-reaction chambers (120).

18 Claims, 4 Drawing Sheets

(56)        References Cited

U.S. PATENT DOCUMENTS

| | | | |
|---|---|---|---|
| 2012/0046187 A1 | 2/2012 | Baba et al. | |
| 2012/0100551 A1 | 4/2012 | Kojima et al. | |
| 2013/0099143 A1* | 4/2013 | Mogami ........... | G01N 21/6454 |
| | | | 356/244 |

FOREIGN PATENT DOCUMENTS

| | | | |
|---|---|---|---|
| CN | 102356319 A | | 2/2012 |
| CN | 108624478 A | | 10/2018 |
| CN | 109234158 | * | 1/2019 |
| CN | 110066723 A | | 7/2019 |
| CN | 110068558 A | | 7/2019 |
| KR | 20190105363 A | | 9/2019 |

OTHER PUBLICATIONS

CN202010121512.9 second office action.
PCT/CN2021/071681 international search report and written opinion.

\* cited by examiner 1210     12 (121)
120
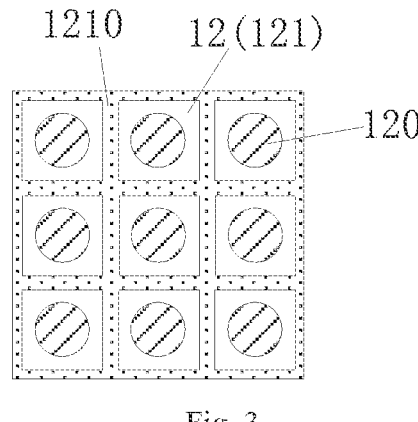
Fig. 3
13
120
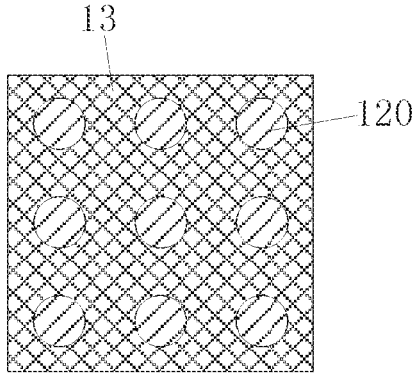
Fig. 4
Reaction system
Detection chip 1
Control device 2
Optical unit 3
Fig. 5

DETECTION CHIP AND MANUFACTURING METHOD THEREFOR, AND REACTION SYSTEM

CROSS REFERENCE TO RELATED APPLICATIONS

The present disclosure is a US National Stage of International Application No. PCT/CN2021/071681, filed on Jan. 14, 2021, which claims the priority of the Chinese Patent Application No. 202010121512.9, filed to the China Patent Office on Feb. 26, 2020 and entitled "Detection Chip and Manufacturing Method therefor, and Reaction System", the entire contents of which are incorporated herein by reference.

FIELD

The present disclosure relates to the technical field of micro-fluidic chips, in particular to a detection chip and a manufacturing method therefor, and a reaction system.

BACKGROUND

The prototype of a digital micro-fluidic chip technology (digital polymerase chain reaction, dPCR) was proposed in 1997 by James F. Brown, Jonathan E. Silver and Olga V. Kalinina. Different from a traditional PCR technology, the dPCR technology fully dilutes nucleic acid samples so that the number of sample templates in each reaction chamber is less than or equal to 1, so as to achieve absolute quantification of single-molecule DNA. Due to its advantages of high sensitivity, strong specificity, high detection throughput, accurate quantification and the like, it is widely used in the aspects like clinical diagnosis, gene instability analysis, single-cell gene expression, environmental microbial detection, and prenatal diagnosis.

SUMMARY

An embodiment of the present disclosure provides a detection chip, including: a first substrate: a microcavity defining layer, located on the first substrate and defining a plurality of micro-reaction chambers; and a shading structure layer, located on the first substrate and disposed among the plurality of micro-reaction chambers.

Optionally, the microcavity defining layer includes an interval portion located among the plurality of micro-reaction chambers, and the interval portion includes a groove disposed around the micro-reaction chambers; and the shading structure layer includes a first portion disposed in the groove.

Optionally, the groove is a through groove penetrating through the interval portion.

Optionally, a cross section of the groove gradually becomes smaller along a direction toward the first substrate.

Optionally, the microcavity defining layer includes the interval portion located among the plurality of micro-reaction chambers; and the shading structure layer includes a second portion covering the interval portion.

Optionally, an orthographic projection of the second portion on the first substrate coincides with an orthographic projection of a side surface, facing away from the first substrate, of the interval portion on the first substrate.

Optionally, the detection chip further includes a hydrophilic layer, and the hydrophilic layer covers inner walls of the plurality of micro-reaction chambers and the shading structure layer.

Optionally, a material of the microcavity defining layer includes a photoresist.

Optionally, a material of the shading structure layer includes a black matrix material.

Optionally, the detection chip further includes a heating electrode; the heating electrode is located on the first substrate and between the microcavity defining layer and the first substrate, and is configured to heat the plurality of micro-reaction chambers; and orthographic projections of the plurality of micro-reaction chambers on the first substrate are located within an orthographic projection of the heating electrode on the first substrate.

Optionally, the detection chip further includes a control electrode and a first insulating layer; the control electrode is located on the first substrate, the first insulating layer covers the control electrode, and the heating electrode is located on the first insulating layer; and the first insulating layer includes a via hole penetrating through the first insulating layer, the control electrode and the heating electrode are electrically connected through the via hole, and the control electrode is configured to apply an electrical signal to the heating electrode.

Optionally, the detection chip further includes a second insulating layer, and the second insulating layer is located between the heating electrode and the microcavity defining layer.

Optionally, the detection chip further includes: a second substrate, disposed opposite to the first substrate; and a hydrophobic layer, covering one side, facing the first substrate, of the second substrate; and the microcavity defining layer and the shading structure layer are located on one side, facing the second substrate, of the first substrate.

Optionally, the first substrate and the second substrate are glass substrates.

Optionally, the first substrate includes a reaction region and a peripheral region, and the peripheral region at least partially surrounds the reaction region; and a size of the second substrate is smaller than that of the first substrate, and an orthographic projection of the second substrate on the first substrate covers the reaction region.

Optionally, the detection chip further includes a plurality of spacers, and the plurality of spacers are disposed at least in the peripheral region and between the first substrate and the second substrate.

Optionally, the detection chip further includes at least one sample inlet and at least one sample outlet, and the sample inlet and the sample outlet each penetrate through the second substrate and the hydrophobic layer.

In another aspect, an embodiment of the present disclosure further provides a reaction system, including the detection chip as described in any one of the above.

In another aspect, an embodiment of the present disclosure further provides a manufacturing method for a detection chip, including: preparing a microcavity defining layer and a shading structure layer on a first substrate; where the microcavity defining layer defines a plurality of micro-reaction chambers, and the shading structure layer is disposed among the plurality of micro-reaction chambers.

Optionally, the preparing the microcavity defining layer and the shading structure layer on the first substrate, specifically includes: preparing a photoresist material layer on the first substrate, where the photoresist material layer includes a plurality of chamber portions for forming the plurality of micro-reaction chambers and an interval portion located among the plurality of chamber portions; forming a pattern of a groove in the interval portion through a first patterning process, where the groove is located among the plurality of chamber portions and disposed around the chamber portions: preparing a black matrix material layer on the photoresist material layer, where the black matrix material layer covers the photoresist material layer and fills the groove; and etching the black matrix material layer and the photoresist material layer through a second patterning process, to enable the plurality of chamber portions of the photoresist material layer to form a pattern of the plurality of micro-reaction chambers, and complete patterning of the black matrix material layer and the photoresist material layer; where the black matrix material layer includes a first portion disposed in the groove and a second portion covering the interval portion of the photoresist material layer.

BRIEF DESCRIPTION OF THE DRAWINGS

FIG. 3 is a partial schematic front view of a detection chip provided by an embodiment of the present disclosure.

FIG. 4 is a partial schematic front view of another detection chip provided by an embodiment of the present disclosure.

FIG. 5 is a structural block diagram of a reaction system provided by an embodiment of the present disclosure.

DETAILED DESCRIPTION OF THE EMBODIMENTS

So far, many companies such as Fluidigm, Thermo Fisher, and Bio-Rad have successively launched dPCR products, and these products have shown huge technical advantages and business prospects in research fields such as single-cell analysis, early cancer diagnosis and prenatal diagnosis. At present, most of the existing products use silicon-based processing or require a tight droplet preparation system, resulting in high cost of chips and complex processing. A glass-based micromachining method combined with a semiconductor technology can produce such chips on a large scale, so that the corresponding preparation cost can be greatly reduced.

An existing glass-based digital micro-fluidic chip generally adopts an excitation light source to be incident in micro-reaction chambers, and detects the fluorescence in each chamber from the front of the chip, that is, fluorescence images are collected from the front of the chip to perform data analysis. Therefore, the signal-to-noise ratio of image acquisition is an important factor to determine the accuracy of the final data analysis.

Embodiments of the present disclosure provide a detection chip and a manufacturing method therefor, and a reaction system. The detection chip is helpful for improving the signal-to-noise ratio of fluorescence image acquisition, and thus improving the accuracy of data analysis of the digital micro-fluidic chip.

The technical solutions of the embodiments of the present disclosure will be described clearly and completely with reference to the accompanying drawings of the embodiments of the present disclosure. Apparently, the described embodiments are some, but not all, embodiments of the present disclosure. Based on the described embodiments of the present disclosure, all other embodiments attainable by those ordinarily skilled in the art without involving any inventive effort are within the protection scope of the present disclosure.

Figure 1:
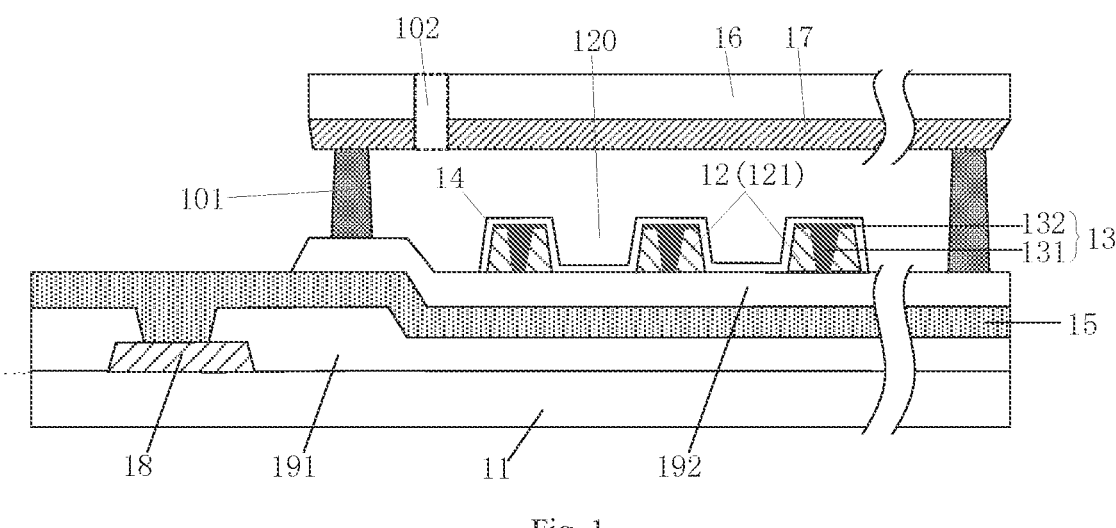
FIG. 1 is a partial schematic cross-sectional view of a detection chip provided by an embodiment of the present disclosure.
Figure 2:
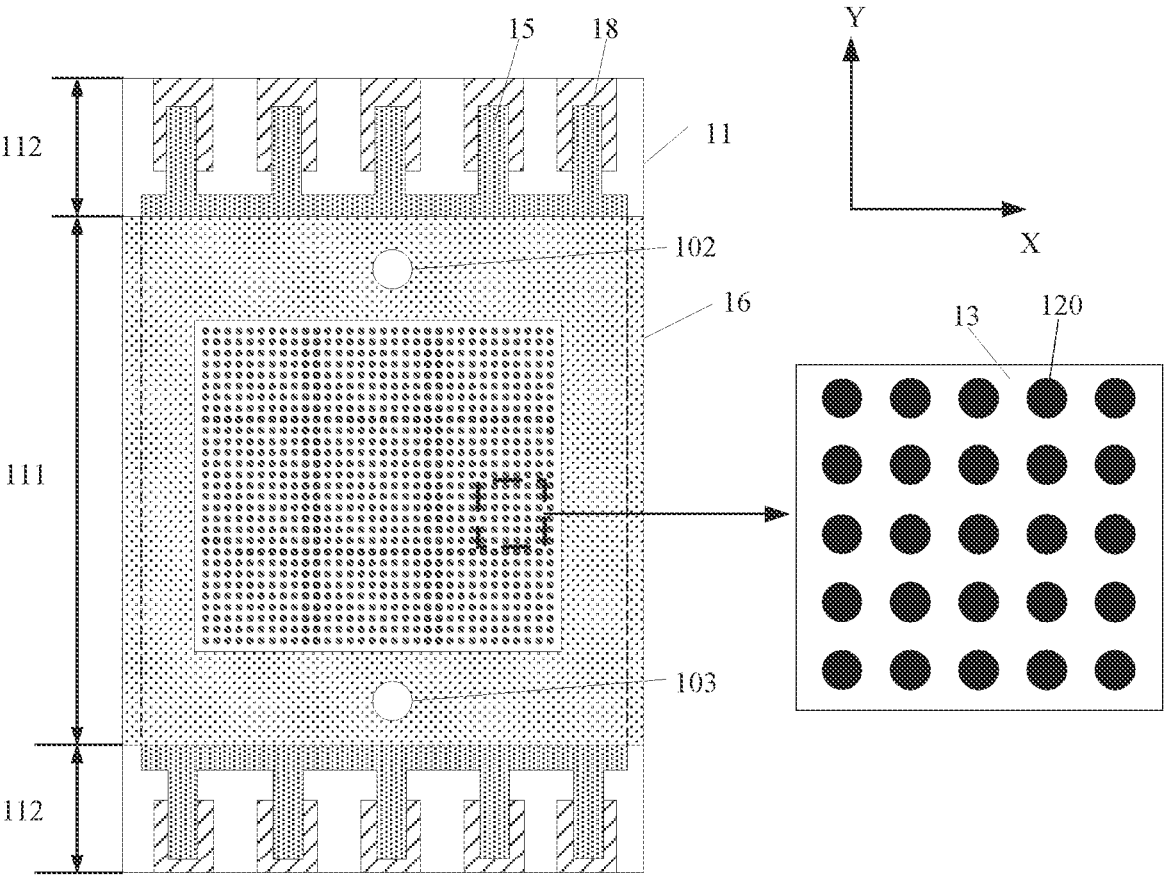
FIG. 2 is a schematic front view of a detection chip provided by an embodiment of the present disclosure.

As shown in FIG. 1 and FIG. 2, embodiments of the present disclosure provide a detection chip. The detection chip includes: a first substrate 11; a microcavity defining layer 12, located on the first substrate 11 and defining a plurality of micro-reaction chambers 120; and a shading structure layer 13, located on the first substrate 11 and disposed among the plurality of micro-reaction chambers 120.

The above-mentioned detection chip provided by the embodiments of the present disclosure may be configured to perform a polymerase chain reaction (e.g., a digital polymerase chain reaction), and may be further configured for the detection process after the reaction.

Specifically, for example, when the detection chip is in practical application, a diluted reaction system solution is injected into the micro-reaction chambers 120 of the detection chip by a sample injection operation, and then an excitation light source is adopted to be incident from the back (the side of, facing away from the microcavity defining layer 12, the first substrate 11) or the front (the side of the first substrate 11 with the microcavity defining layer 12) of the detection chip, the fluorescence is detected from the front of the detection chip, and data analysis is performed on a fluorescence image collected from the front of the chip, to judge the number of target molecules in the reaction system solution in each micro-reaction chamber 120. The detection chip includes the shading structure layer 13, and the shading structure layer 13 is located on the first substrate 11 and is disposed among the plurality of micro-reaction chambers 120, so that fluorescence crosstalk between adjacent micro-reaction chambers 120 can be suppressed, so as to the single-to-noise ratio of fluorescence image acquisition, and thus improve the accuracy of data analysis.

Specifically, in the detection chip provided by the embodiments of the present disclosure, the first substrate 11 plays a role of protection, support and the like. The microcavity defining layer 12 is located on the first substrate 11 and configured to define the plurality of micro-reaction chambers 120. Shapes of the plurality of micro-reaction chambers 120 may be the same, and a three-dimensional shape of each micro-reaction chamber 120 may be an approximate cylinder. For example, a diameter of the bottom surface of the cylinder ranges from 1 micron to 100 microns and a height of the cylinder ranges from 5 microns to 100 microns. In some examples, the diameter of the bottom surface of the cylinder is 8 microns and the height of the cylinder is 9.8 microns. It should be noted that the shapes of at least part of the micro-reaction chambers 120 may also be different. Or, the shapes of the micro-reaction chambers 120 may be designed according to actual requirements. For example, the shape of each micro-reaction chamber 120 may also be a frustum of a cone, a cuboid, a polygonal prism, a sphere, an ellipsoid and the like, which is not limited in the embodiments of the present disclosure.

Specifically, the plurality of micro-reaction chambers 120 are uniformly distributed on the first substrate 11. For example, on the first substrate 11, the plurality of micro-reaction chambers 120 are arranged in an array in a first direction X and a second direction Y, and the first direction X and the second direction Y are perpendicular to each other. In this way, the fluorescent image obtained when the detection chip is optically detected in the subsequent stage is more regular and neat, so that a detection result can be obtained quickly and accurately. Of course, the embodiments of the present disclosure are not limited thereto, and the plurality of micro-reaction chambers 120 may also be unevenly distributed on the first substrate 11 or in other arrangement modes, which are not limited in the embodiments of the present disclosure. For example, the number of the plurality of micro-reaction chambers 120 may be 2,000-1,000,000. For example, in some examples, the number of the plurality of micro-reaction chambers 120 is 40,000-100,000. There-fore, the detection throughput of the detection chip is large.

Since the target molecules (namely DNA templates) in the reaction system solution are sufficiently diluted, after the reaction system solution enters each micro-reaction chamber 120, the number of the target molecule (namely the DNA templates) in each micro-reaction chamber 120 is less than or equal to 1. That is, each micro-reaction chamber 120 includes only one target molecule or no target molecule, to obtain the accurate detection result in the subsequent stage.

Specifically, a material of the microcavity defining layer 12 includes a photoresist. For example, the material of the microcavity defining layer 12 is a photoresist that can use a thick film process. The photoresist may be formed on the first substrate 11 by spin coating, and has a relatively large thickness. For example, the thickness of the microcavity defining layer 12 may range from 5 microns to 100 microns, for example, 9.8 microns. For example, the microcavity defining layer 12 may be patterned and etched, thereby obtaining the plurality of micro-reaction chambers 120, and the plurality of micro-reaction chambers 120 are disposed at intervals.

As shown in FIG. 1 and FIG. 3, in some embodiments, the microcavity defining layer 12 includes an interval portion 121 located among the plurality of micro-reaction chambers 120, and the interval portion 121 includes a groove 1210 located among the plurality of micro-reaction chambers 120 and around the micro-reaction chambers 120. The shading structure layer 13 includes a first portion 131 disposed in the groove 1210.

It should be noted that, in the present disclosure, "among the plurality of micro-reaction chambers" not only includes a region between adjacent micro-reaction chambers, but also may include a region adjacent to the outer edges of the micro-reaction chambers at the edge; that is, a region on the side, away from the inner micro-reaction chambers, of the micro-reaction chambers at the edge may also be included. In other words, the interval portion and the groove of the microcavity defining layer not only surround the inner micro-reaction chambers, but also the micro-reaction cham-bers at the edge.

For example, the interval portion 121 of the microcavity defining layer 12 defines and surrounds the micro-reaction chambers 120, the groove 1210 formed in the interval portion 121 is grid-shaped, and each grid has one micro-reaction chamber 120. The first portion 131 of the shading structure layer 13 is disposed in the groove 1210 and is also grid-shaped. Each grid formed by the first portion 131 of the shading structure layer 13 surrounds one micro-reaction chamber 120.

The groove 1210 is disposed in the interval portion 121 of the microcavity defining layer 12, and the first portion 131 of the shading structure layer 13 is disposed in the groove 1210, and the micro-reaction chambers 120 may be sepa-rated by the first portion 131 of the shading structure layer 13, to avoid fluorescence crosstalk between adjacent micro-reaction chambers 120. Thus, the signal-to-noise ratio of fluorescence image acquisition can be improved, and the accuracy of data analysis is further improved.

Exemplarily, the groove 1210 may be a through groove penetrating through the microcavity defining layer 12, i.e., the interval portion 121, so that the first portion 131 of the shading structure layer 13 located in the groove 1210 may penetrate through the microcavity defining layer 12, and the micro-reaction chambers 120 may be completely separated. Of course, the groove 1210 may also not be a through groove, and its specific depth may be determined according to actual requirements, for example, it may be approxi-mately equal to a depth of the micro-reaction chambers 120.

Exemplarily, a longitudinal section of the groove 1210 is an inverted trapezoid, that is, a cross section of the groove 1210 gradually becomes smaller along a direction toward the first substrate 11. Therefore, on one hand, the processing of the grooves 1210 is facilitated, and on the other hand, the first portion 131 of the shading structure layer 13 may completely fill the groove 1210, to avoid an air layer and affect the quality of the fluorescent image.

As shown in FIGS. 1, 3 and 4, in some embodiments, the microcavity defining layer 12 includes the interval portion 121 located among the plurality of micro-reaction chambers 120. The shading structure layer 13 includes a second portion 132 covering the interval portion 121.

Exemplarily, the shading structure layer 13 may only include the second portion 132 covering the interval portion 121 of the microcavity defining layer 12. Or, the shading structure layer 13 may include both the second portion 132 covering the interval portion 121 and the first portion 131 disposed in the groove.

Exemplarily: an orthographic projection of the second portion 132 on the first substrate 11 coincides with an orthographic projection of a side surface, facing away from the first substrate 11, of the interval portion 121 on the first substrate 11.

The shading structure layer 13 completely covers the side surface, facing away from the first substrate 11, of the interval portion 121 of the microcavity defining layer 12, and exposes each micro-reaction chamber 120; then the fluorescence can only be transmitted through an opening of each micro-reaction chamber 120. In this way, the resolution and contrast of the fluorescence image can be effectively improved, the signal-to-noise ratio of fluorescence image acquisition can be improved, and thus the accuracy of data analysis is improved.

As shown in FIG. 1, in some embodiments, the detection chip further includes a hydrophilic layer 14; and the hydro-philic layer 14 has hydrophilic and oleophobic properties.

Exemplarily, the hydrophilic layer 14 covers the inner walls of the plurality of micro-reaction chambers 120, so that the inner surfaces of the micro-reaction chambers 120 have higher hydrophilicity. In the absence of an external driving force on the reaction system solution, the reaction system solution may automatically and gradually enter each micro-reaction chamber 120 based on a capillary phenom-enon, thereby realizing automatic sample injection.

Exemplarily, the hydrophilic layer 14 may also cover the shading structure layer 13, that is, the hydrophilic layer 14 simultaneously covers the inner walls of the plurality of micro-reaction chambers 120 and the shading structure layer 13 among the plurality of micro-reaction chambers 120. In this way, the hydrophilic layer 14 may completely cover the microcavity defining layer 12 and the shading structure layer 13, so that the reaction system solution can more easily enter each micro-reaction chamber 120, and the sample injection speed can be increased.

A material of the hydrophilic layer 14 is generally silicon oxide, such as silicon dioxide (SiO2). Of course, the embodiments of the present disclosure are not limited thereto, and the hydrophilic layer 14 may also be prepared by using other suitable inorganic or organic materials, as long as it is guaranteed that a surface, away from the microcavity defining layer 12, of the hydrophilic layer 14 is hydrophilic.

In some embodiments, a material of the shading structure layer 13 may include a black matrix material. The black matrix material has a good shading effect, which can improve the resolution and contrast of the fluorescent image, effectively improve the signal-to-noise ratio of fluorescent image acquisition, and improve the accuracy of data analysis.

As shown in FIG. 1 and FIG. 2, in some embodiments, the detection chip further includes a heating electrode 15; and the heating electrode 15 is located on the first substrate 11, disposed between the microcavity defining layer 12 and the first substrate 11, and configured to heat the plurality of micro-reaction chambers 120. Orthographic projections of the plurality of micro-reaction chambers 120 on the first substrate 11 are located within an orthographic projection of the heating electrode 15 on the first substrate 11. Here, the orthographic projection refers to a projection on the first substrate 11 in a direction perpendicular to the first substrate 11.

The microcavity defining layer 12 and the heating electrode 15 are both located on the first substrate 11; the microcavity defining layer 12 defines the plurality of micro-reaction chambers 120; and the heating electrode 15 is closer to the first substrate 11 than the microcavity defining layer 12, and is configured to heat the plurality of micro-reaction chambers 120.

The heating electrode 15 may receive an electrical signal (e.g., a voltage signal), whereby heat is generated when an electric current flows through the heating electrode 15, and the heat is conducted into the micro-reaction chambers 120 for the polymerase chain reaction. For example, the heating electrode 15 may be made of a conductive material with a relatively high resistivity, so that the heating electrode 15 can generate a relatively large amount of heat while providing a relatively small electrical signal, so as to improve the energy conversion rate. The heating electrode 15 may be made of a transparent conductive material, so that laser can be incident into the micro-reaction chambers 120 from the back of the chip, for example, the heating electrode 15 is made of indium tin oxide (ITO), tin oxide and the like. Of course, the heating electrode 15 may also be made of other suitable materials, for example, metal and other non-transparent materials. At this moment, the laser may be incident into the micro-reaction chambers 120 from the front of the chip. Specifically, the embodiments of the present disclosure do not limit the material of the heating electrode 15. For example, the heating electrode 15 is a planar electrode, which is uniformly formed on the first substrate 11 by using the conductive material, so that a plurality of micro-reaction chambers 120 are heated evenly.

In the embodiments of the present disclosure, by arranging the heating electrode 15 in the detection chip (for example, integrating the heating electrode 15 on the first substrate 11), the heating of the micro-reaction chambers 120 of the detection chip can be effectively realized, so that the temperature control of the micro-reaction chambers 120 is realized, external heating equipment is not required, and the integration is high. Moreover, compared with some detection chips that need to drive droplets to move and pass through a plurality of temperature regions in sequence, the detection chip can realize temperature cycling without driving the droplets, operation is simple and a production cost is low.

As shown in FIG. 1, in some embodiments, the detection chip further includes a second substrate 16 and a hydrophobic layer 17. The second substrate 16 is disposed opposite to the first substrate 11; and the hydrophobic layer 17 covers one side, facing the first substrate 11, of the second substrate 16. The microcavity defining layer 12 and the shading structure layer 13 are located on one side, facing the second substrate 16, of the first substrate 11.

The hydrophobic layer 17 has hydrophobic and lipophilic properties; and is located on one side, facing the first substrate 11, of the second substrate 16. The microcavity defining layer 12 is located on the side, facing the second substrate 16, of the first substrate 11. By disposing the hydrophobic layer 17, the reaction system solution may more easily enter into each micro-reaction chamber 120 defined by the microcavity defining layer 12.

A material of the hydrophobic layer 17 may be resin or silicon nitride, for example, may be a commercially available epoxy resin with a model of DL-1001C. The hydrophobic layer 17 may also be prepared by using other suitable inorganic or organic materials, as long as it is guaranteed that one side, facing the first substrate 11, of the hydrophobic layer 17 has hydrophobicity.

In the embodiments of the present disclosure, the hydrophilic layer 14 and the hydrophobic layer 17 may jointly adjust the contact angle of the surface of the droplets of the reaction system solution, thereby enabling the detection chip to realize self-absorption liquid injection and oil sealing. For example, in the detection chip, the hydrophobicity of the structure on the side opposite to the microcavity defining layer 12 (e.g., the surface, facing the micro-reaction chambers 120, of the second substrate 16) is improved by the hydrophobic layer 17, so that the outside of the micro-reaction chambers 120 is hydrophobic; and the hydrophilicity of the inner surfaces of the micro-reaction chambers 120 is improved through the hydrophilic layer 14, so that the reaction system solution infiltrates from the outside of the micro-reaction chambers 120 to the inside of the micro-reaction chambers 120. Therefore, under the combined action of the hydrophilic layer 14 and the hydrophobic layer 17, the reaction system solution may more easily enter each micro-reaction chamber 120.

In some embodiments, the first substrate 11 and the second substrate 16 are glass substrates.

The detection chip may be prepared by a glass-based micromachining method combined with a semiconductor technology, so that large-scale mass production can be achieved, and a corresponding production cost can be greatly reduced. It should be noted that, in multiple embodiments of the present disclosure, the first substrate 11 and the second substrate 16 may also be other suitable substrates, which are not limited in the embodiments of the present disclosure.

Specifically, as shown in FIG. 1 and FIG. 2, the shape of the first substrate 11 and a shape of the second substrate 16 may both be rectangular. For example, in some examples, a size of the first substrate 11 is 3.2 cm*4.5 cm, and a size of the second substrate 16 is 3.2 cm*3 cm.

As shown in FIG. 2, in some embodiments, the first substrate 11 includes a reaction region 111 and a peripheral region 112, and the peripheral region 112 at least partially surrounds the reaction region 111.

Exemplarily, the size of the second substrate 16 is smaller than that of the first substrate 11, and the second substrate 16 covers the reaction region 111, for example, an orthographic projection of the second substrate 16 on the first substrate 11 may completely overlap the reaction region 111. It should be noted that the embodiments of the present disclosure are not limited thereto, and in some other examples, the size of the second substrate 16 may also be the same as that of the first substrate 11.

As shown in FIG. 1 and FIG. 2, in some embodiments, the detection chip further includes a plurality of spacers 101. The plurality of spacers 101 are disposed in the peripheral region 112 and between the first substrate 11 and the second substrate 16. The plurality of spacers 101 are configured to maintain a distance between the first substrate 11 and the second substrate 16 to provide space for the flow of the reaction system solution. For example, in some embodiments, a part of the spacers 101 may also be disposed in the reaction region 111, for example, distributed in a plurality of positions in the reaction region 111, to improve the compressive strength of the detection chip and prevent the reaction region from being subjected to external force to cause damage of the detection chip.

The first substrate 11, the microcavity defining layer 12, a sealant including the spacers 101, and the second substrate 16 jointly define a sample injection channel and a sample outlet channel for the droplets of the reaction system solution, thereby ensuring that the droplets can move to each micro-reaction chamber 120 and the droplets that do not enter the micro-reaction chambers 120 flow out of the space between the first substrate 11 and the second substrate 16.

Exemplarily, as shown in FIG. 1 and FIG. 2, the detection chip includes at least one sample inlet 102 and at least one sample outlet 103, and the sample inlet 102 and the sample outlet 103 each penetrate through the second substrate 16 and the hydrophobic layer 17. The reaction system solution may be injected into the sample inlet 102 through a micro-syringe pump or a pipette, and then enters each micro-reaction chamber 120 through self-priming; and the droplets that do not enter the micro-reaction chambers 120 flow out of the space between the first substrate 11 and the second substrate 16 through the sample outlet 103.

As shown in FIG. 1 and FIG. 2, in some embodiments, the detection chip further includes a control electrode 18 and a first insulating layer 191. The control electrode 18 is located on the first substrate 11, the first insulating layer 191 covers the control electrode 18, and the heating electrode 15 is located on the first insulating layer 191. For example, the first insulating layer 191 includes a via hole penetrating through the first insulating layer 191, and the control electrode 18 and the heating electrode 15 are electrically connected through the via hole, and the control electrode 18 is configured to apply the electrical signal (e.g., the voltage signal) to the heating electrode 15. After the heating electrode 15 receives the electrical signal, heat is generated under the action of the electrical signal, thereby heating the micro-reaction chambers 120.

As shown in FIG. 1, in some embodiments, the detection chip further includes a second insulating layer 192. The second insulating layer 192 is located between the heating electrode 15 and the microcavity defining layer 12. The second insulating layer 192 is configured to protect the heating electrode 15, provide insulation, prevent liquid from corroding the heating electrode 15, and slow down the aging of the heating electrode 15; and the second insulating layer 192 may play a role of planarization.

The first insulating layer 191 and the second insulating layer 192 may be prepared by using the same insulating material, for example, an inorganic insulating material or an organic insulating material. For example, materials of the first insulating layer 191 and the second insulating layer 192 are silicon dioxide or silicon nitride, etc.

Based on the same inventive concept, as shown in FIG. 5, embodiments of the present disclosure further provide a reaction system, which includes the detection chip 1 as described in any one of the above.

In some embodiments, the reaction system further includes a control device 2; and the control device 2 is electrically connected to the detection chip 1, and is configured to apply an electrical signal to the detection chip 1 to drive the heating electrode of the detection chip 1.

In some embodiments, the reaction system may further include an optical unit 3 configured to perform optical detection on the detection chip 1. Exemplarily, the optical unit 3 includes a fluorescence detection device, and the fluorescence detection device is configured to perform fluorescence detection on a solution to be detected in a plurality of micro-reaction chambers. For example, the fluorescence detection device may include a fluorescence light source and an image sensor (e.g., a charge coupled device (CCD) image sensor). It should be noted that the "solution to be detected" is a solution after a polymerase chain reaction is performed on a reaction system solution, that is, the reaction system solution after an amplification reaction is completed. Exemplarily, the optical unit 3 may further include an image processing device, and the image processing device is configured to process a detection picture output by the fluorescence detection device. For example, the image processing device may include a central processing unit (CPU) or a graphics processing unit (GPU), or the like. For example, the control device 2 is also configured to control the fluorescence detection device and the image processing device to perform corresponding functions.

Based on the same inventive concept, embodiments of the present disclosure further provide a manufacturing method for a detection chip. The method includes the following step: a microcavity defining layer and a shading structure layer are prepared on a first substrate. The microcavity defining layer defines a plurality of micro-reaction chambers, and the shading structure layer is disposed among the plurality of micro-reaction chambers.

In some embodiments, the step of preparing the microcavity defining layer and the shading structure layer on the first substrate may specifically include the following steps.

Figure 6A:
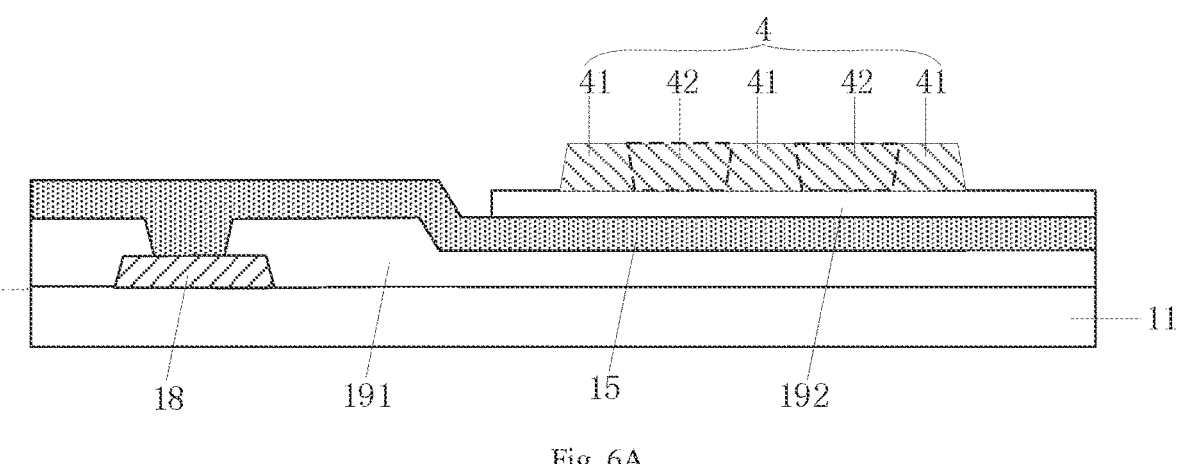
FIGS. 6A-6E is a schematic cross-sectional view in a manufacturing process of a detection chip provided by an embodiment of the present disclosure.

Step 101, as shown in FIG. 6A, a photoresist material layer 4 is prepared on the first substrate 11, and the photoresist material layer 4 includes a plurality of chamber portions 42 for forming the plurality of micro-reaction chambers and interval portions 41 located among the plurality of chamber portions 42.

Figure 6B:
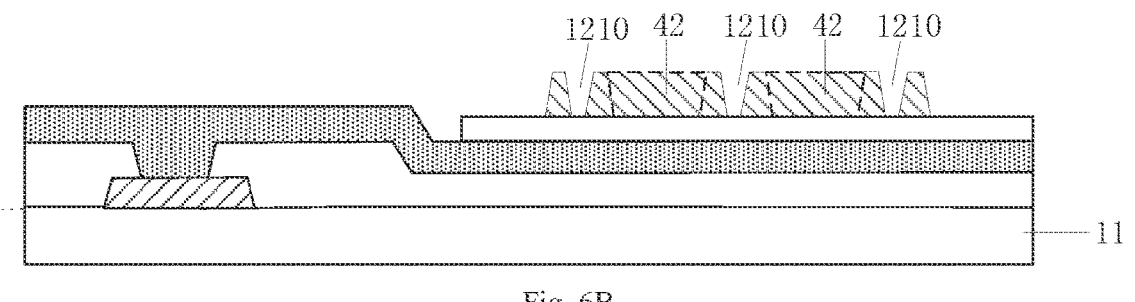

Step 102, as shown in FIGS. 6A-6B, patterns of grooves 1210 are formed in the interval portions 41 through a first patterning process, and the grooves 1210 are located among the plurality of chamber portions 42 and disposed around the chamber portions 42.

Figure 6C:
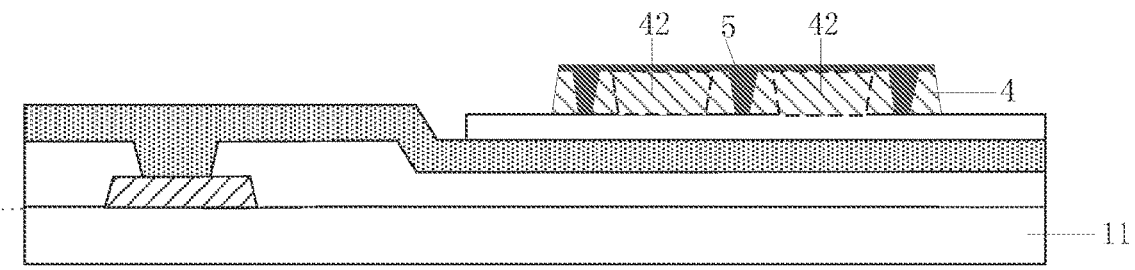

Step 103, as shown in FIGS. 6B-6C, a black matrix material layer 5 is prepared on the photoresist material layer 4, and the black matrix material layer 5 covers the photoresist material layer 4 and fills the grooves 1210.

Figure 6D:
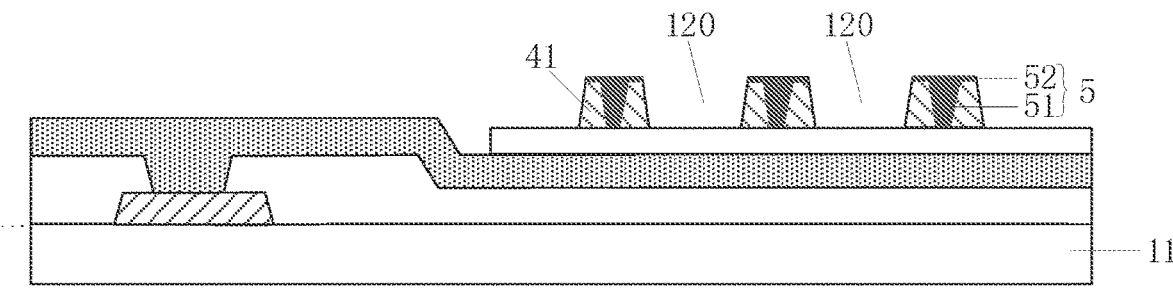

Step 104, as shown in FIGS. 6C-6D, the black matrix material layer 5 and the photoresist material layer 4 are etched through a second patterning process, to enable each chamber portion 42 of the photoresist material layer 4 to form a pattern of the micro-reaction chamber 120, and complete patterning of the black matrix material layer 5 and the photoresist material layer 4; and the black matrix material layer 5 includes first portions 51 disposed in the grooves and second portions 52 covering the interval portions 41 of the photoresist material layer 4.

Figure 6E:
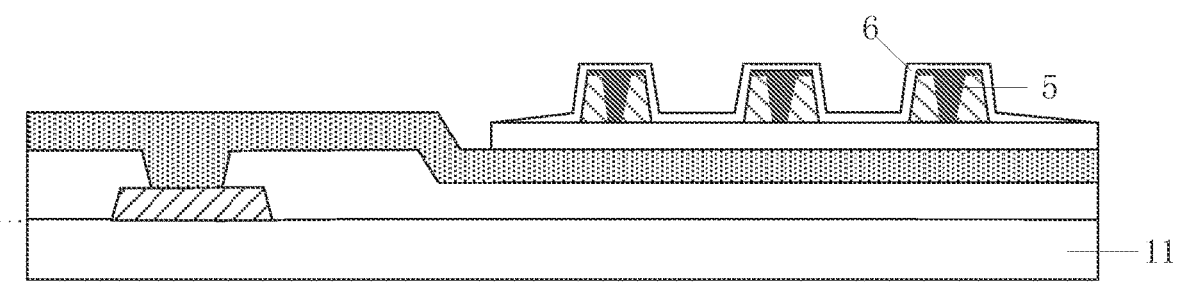

In some embodiments, after preparing the microcavity defining layer and the shading structure layer on the first substrate, the following steps may also be included: as shown in FIGS. 6D-6E, a hydrophilic layer 6 is prepared on the shading structure layer 5. Specifically, the hydrophilic layer 6 may cover the inner walls of the plurality of micro-reaction chambers 120 and the black matrix material layer 5.

In some embodiments, before preparing the microcavity defining layer and the shading structure layer on the first substrate, the method may also include the steps of sequentially preparing a control electrode 18, a first insulating layer 191, a heating electrode 15 and a second insulating layer 192 on the first substrate shown in FIG. 6A.

It should be noted that, in some embodiments of the present disclosure, the manufacturing method for the detection chip may also include more steps, which may be determined according to the actual requirements, the embodiments of the present disclosure are not limited thereto, and detailed description and technical effects may refer to the above description of the detection chip and the reaction system, which will not be repeated here. In addition, in the manufacturing method for the detection chip, the "preparing the microcavity defining layer and the shading structure layer on the first substrate" is not limited to the above-mentioned embodiments, and other methods and steps may also be used, which may specifically refer to the above description of the structure of the microcavity defining layer and the shading structure layer of the detection chip, which will not be repeated here.

It will be apparent to those skilled in the art that various modifications and variations can be made in the embodiments of the present disclosure without departing from the spirit or scope of the present disclosure. Thus, if these modifications and variations of the present disclosure fall within the scope of the claims of the present disclosure and its equivalent technology, the present disclosure is also intended to include these modifications and variations.

What is claimed is:

1. A detection chip, comprising:
a first substrate;
a microcavity defining layer, arranged on the first substrate and defining a plurality of micro-reaction chambers; and
a shading structure layer, arranged on the first substrate and disposed among the plurality of micro-reaction chambers;
wherein the microcavity defining layer comprises an interval portion arranged among the plurality of micro-reaction chambers;
the interval portion comprises a groove disposed around the plurality of micro-reaction chambers;
the shading structure layer comprises a first portion disposed in the groove;
the groove is a through groove penetrating through the interval portion; and
the first portion disposed in the groove penetrates through the interval portion.

2. The detection chip according to claim 1, wherein a cross section of the groove gradually becomes smaller along a direction toward the first substrate.

3. The detection chip according to claim 1, wherein the microcavity defining layer comprises an interval portion arranged among the plurality of micro-reaction chambers; and
the shading structure layer comprises a second portion covering the interval portion.

4. The detection chip according to claim 3, wherein an orthographic projection of the second portion on the first substrate coincides with an orthographic projection of a side surface, facing away from the first substrate, of the interval portion on the first substrate.

5. The detection chip according to claim 3, further comprising a hydrophilic layer;
wherein the hydrophilic layer covers inner walls of the plurality of micro-reaction chambers and the shading structure layer.

6. The detection chip according to claim 3, wherein a material of the microcavity defining layer comprises a photoresist.

7. The detection chip according to claim 3, wherein a material of the shading structure layer comprises a black matrix material.

8. The detection chip according to claim 3, further comprising a heating electrode;
wherein the heating electrode is arranged on the first substrate and between the microcavity defining layer and the first substrate, and is configured to heat the plurality of micro-reaction chambers; and
orthographic projections of the plurality of micro-reaction chambers on the first substrate are arranged within an orthographic projection of the heating electrode on the first substrate.

9. The detection chip according to claim 8, further comprising a control electrode and a first insulating layer;
wherein the control electrode is arranged on the first substrate, the first insulating layer covers the control electrode, and the heating electrode is arranged on the first insulating layer; and
the first insulating layer comprises a via hole penetrating through the first insulating layer, the control electrode and the heating electrode are electrically connected through the via hole, and the control electrode is configured to apply an electrical signal to the heating electrode.

10. The detection chip according to claim 9, further comprising a second insulating layer;
wherein the second insulating layer is arranged between the heating electrode and the microcavity defining layer.

11. The detection chip according to claim 4, further comprising:
a second substrate, disposed opposite to the first substrate; and
a hydrophobic layer, covering one side, facing the first substrate, of the second substrate;
wherein the microcavity defining layer and the shading structure layer are arranged on one side, facing the second substrate, of the first substrate.

12. The detection chip according to claim 11, wherein the first substrate and the second substrate are glass substrates.

13. The detection chip according to claim 11, wherein the first substrate comprises a reaction region and a peripheral region, and the peripheral region at least partially surrounds the reaction region; and a size of the second substrate is smaller than that of the first substrate, and an orthographic projection of the second substrate on the first substrate covers the reaction region.

14. The detection chip according to claim 13, further comprising a plurality of spacers;

wherein the plurality of spacers are disposed at least in the peripheral region and between the first substrate and the second substrate.

15. The detection chip according to claim 11, further comprising at least one sample inlet and at least one sample outlet;

wherein the at least one sample inlet and the at least one sample outlet each penetrate through the second substrate and the hydrophobic layer.

16. A reaction system, comprising the detection chip according to claim 1.

17. A manufacturing method for the detection chip according to claim 1, comprising:

preparing the microcavity defining layer and the shading structure layer on the first substrate.

18. The manufacturing method according to claim 17, wherein the preparing the microcavity defining layer and the shading structure layer on the first substrate, specifically comprises:

preparing a photoresist material layer on the first substrate, wherein the photoresist material layer comprises a plurality of chamber portions for forming the plurality of micro-reaction chambers and an interval portion arranged among the plurality of chamber portions;

forming a pattern of a groove in the interval portion through a first patterning process, wherein the groove is arranged among the plurality of chamber portions and disposed around the plurality of chamber portions;

preparing a black matrix material layer on the photoresist material layer, wherein the black matrix material layer covers the photoresist material layer and fills the groove; and etching the black matrix material layer and the photoresist material layer through a second patterning process, to enable the plurality of chamber portions of the photoresist material layer to form a pattern of the plurality of micro-reaction chambers, and complete patterning of the black matrix material layer and the photoresist material layer;

wherein the black matrix material layer comprises a first portion disposed in the groove and a second portion covering the interval portion of the photoresist material layer.

* * * * *